United States Patent [19]

Fröidh et al.

[11] Patent Number: 4,735,316
[45] Date of Patent: Apr. 5, 1988

[54] PACKAGE FOR INDIVIDUAL, DISPOSABLE SANITARY ARTICLES AND A METHOD OF MANUFACTURING SUCH A PACKAGE

[75] Inventors: Arne Fröidh, Stenungsund; Stewe Alsenvik; Urban Widlund, both of Molnlycke; Carl-Daniel Norenberg, Gothenburg, all of Sweden

[73] Assignee: Molnlycke AB, Gothenburg, Sweden

[21] Appl. No.: 802,213

[22] Filed: Nov. 26, 1985

[30] Foreign Application Priority Data

Nov. 26, 1984 [SE] Sweden ............................ 8405952

[51] Int. Cl.$^4$ ............................................. A61F 13/16
[52] U.S. Cl. ................................. 206/438; 206/440; 206/494; 229/DIG. 3; 383/120; 604/397
[58] Field of Search ............... 206/438, 440, 441, 494, 206/495, 363, 813; 383/2, 120; 604/358, 397, 398, 402; 229/DIG. 3, 87 R

[56] References Cited

U.S. PATENT DOCUMENTS

| | | | |
|---|---|---|---|
| 1,846,584 | 2/1932 | Clark | 229/87 R |
| 1,951,011 | 3/1934 | Falk | 383/120 |
| 2,296,951 | 9/1942 | Rosen et al. | 229/DIG. 3 |
| 2,364,943 | 12/1944 | Brandt | 229/DIG. 3 |
| 2,628,764 | 2/1953 | Rubinstein et al. | 229/DIG. 3 |
| 2,705,104 | 3/1955 | Vogt | 229/87 R |
| 3,024,788 | 3/1962 | Lane . | |
| 3,035,578 | 5/1962 | Elmore | 206/438 |
| 3,058,469 | 10/1962 | Crockford . | |
| 3,674,195 | 7/1972 | Stone | 206/440 |
| 3,717,244 | 2/1973 | Smith | 206/438 |
| 3,973,567 | 8/1976 | Srinivasan et al. | 206/438 |
| 4,182,336 | 1/1980 | Black | 206/438 |
| 4,284,227 | 8/1981 | Corey | 229/DIG. 3 |
| 4,564,108 | 1/1986 | Widlund et al. | 206/438 |

FOREIGN PATENT DOCUMENTS

| | | |
|---|---|---|
| 3146067 | 7/1982 | Fed. Rep. of Germany . |
| 2462351 | 3/1981 | France ............... 206/438 |
| 1564632 | 4/1980 | United Kingdom . |

*Primary Examiner*—David T. Fidei
*Attorney, Agent, or Firm*—Young & Thompson

[57] ABSTRACT

The invention relates principally to a package adapted for disposable sanitary articles, preferably sanitary napkins and incontinence articles, and secondly to a method of manufacturing such a product.

The primary distinguishing feature thereof is that, in a manner known per se, it is designed as a bag of a liquid impervious material, which bag in its packaging stage compactly encloses a disposable article, and that pleats or the like are arranged allowing the bag, after opening and removal of the enclosed article, to expand by one or more pleats spreading out for the accommodation of a used article of the kind in question.

2 Claims, 4 Drawing Sheets

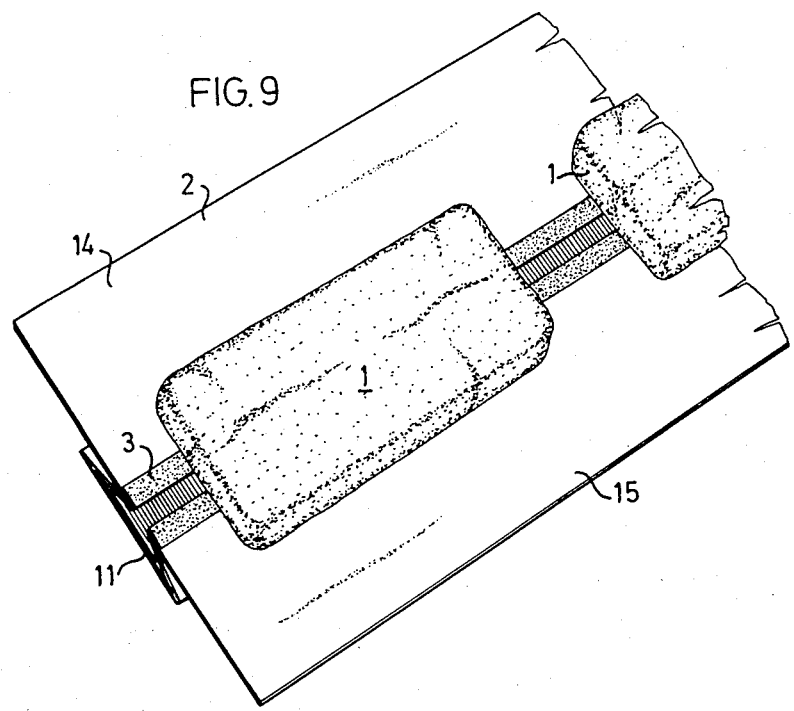
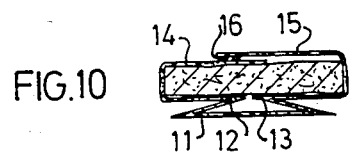
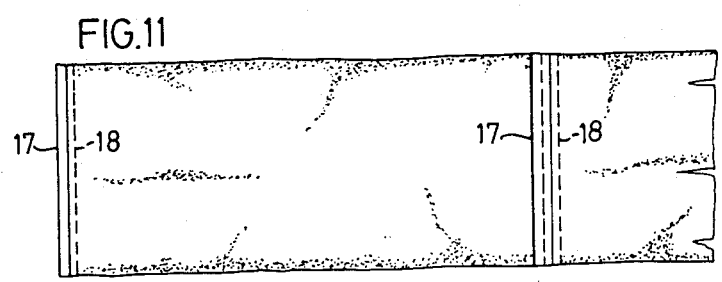

PACKAGE FOR INDIVIDUAL, DISPOSABLE SANITARY ARTICLES AND A METHOD OF MANUFACTURING SUCH A PACKAGE

BACKGROUND OF THE INVENTION

The present invention relates primarily to a package for disposable sanitary articles, preferably sanitary napkins, incontinence articles and the like, and secondly to a method of producing such a package.

Up to now, disposable articles such as diapers, sanitary napkins and the like have generally been loosely packed in large packages such as plastic bags and cartons. When travelling, packages of this type are of course impractical and too bulky in case only a small number of such articles would be required. For this reason there have lately been developed one-piece packages for this kind of sanitary articles. A one-piece package of this type is described in German Laid-open Publication No. 31 46 067 and consists of a plastic film or the like having one end portion folded in over its mid-portion, the side edges of these portions, brought into alignment as a result of the folding, being welded together to form a collecting pocket into which a folded disposable article can be inserted. The opposite end portion of the packing film is adapted to serve as a sealing cover over said pocket, this portion as well being welded along its edges to the edges of said pocket. The cover thus created is furthermore provided with an adhesive bead by means of which the pocket can be resealed after the package has been opened. This one-piece package also has for its purpose to constitute a so-called service bag, i.e. a collecting bag for a used disposable article.

The fact that disposable articles in the form of diapers, sanitary napkins and the like will change their shape and become wet and clumsy after having absorbed body fluids makes it practically impossible to tuck down a used article of the kind in question into this type of prior art packaging and/or service bag.

To this end there exists a great need for enabling disposable articles to be packed in one-piece wrappers, which after use of the article contained therein could also be utilized as service bags for storage of the used article. However, moisture absorbing disposable articles are relatively bulky, and in the packaging process it is of course necessary therefore to keep the packages as compact as possible. So far however, this object has been impossible to combine with the demand of making the packages large enough to be usable as service bags for such articles.

The problems outlined above have however been completely eliminated with the present invention in that a package performed in accordance therewith is primarily distinguished by consisting of one, or a plurality of one-piece parcels arranged with intermediate perforations, each parcel being designed as a bag of liquid impervious material which bag, after opening and taking out an article packed therein, is expandable by means of pleats or the like, arranged in at least one of its walls, being spread out for enabling the bag to accommodate such an article after use.

Some suitable embodiments of a package according to the invention are set forth in claims 1 and 2.

The inventive method of manufacturing packages of this type for disposable sanitary articles, preferably sanitary napkins and incontinence products, are set forth in claims 4, 5 and 6.

The invention will be more closely described in the following while referring to some exemplary embodiments shown in the accompanying drawings.

BRIEF DESCRIPTION OF THE DRAWINGS

FIG. 3 is a cross-sectional view through the finished package, whereas

FIGS. 5–8 illustrate a somewhat modified embodiment of a package made in accordance with the invention, while, FIGS. 9–11 illustrate a third embodiment of a package according to the invention and the manufacturing process of this embodiment.

DESCRIPTION OF THE PREFERRED EMBODIMENTS

Figure 1:
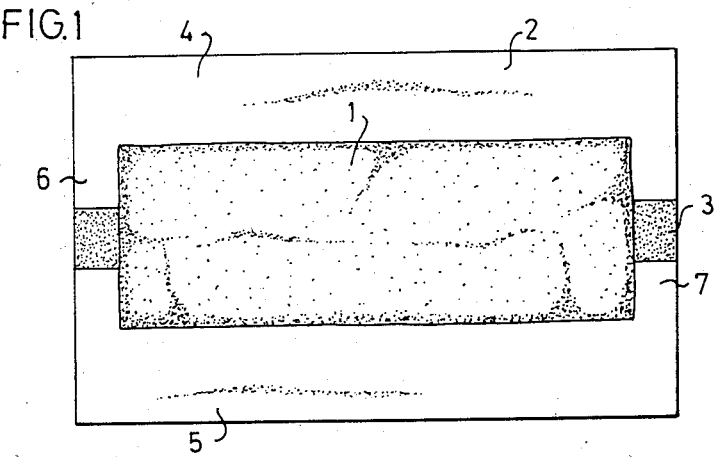
FIG. 1 of the drawings illustrates a package blank with an article to be packed placed upon it.

In FIG. 1, reference numeral 1 designates a sanitary napkin intended to be packed, and reference numeral 2 designates a piece of plastic film serving as a package blank. On its side contacting the plastic film and facing the underpants of the wearer during use, the sanitary napkin is provided with an adhesive coating to keep the napkin fixed in position. This coating, which can consists of hot melt for example, is not illustrated in the drawings. Up to now, the process of packing sanitary napkins provided with an adhesive coating has involved the use of a release paper applied to the coating. As such release papers are however rather expensive in relation to the total cost of the product, they have been replaced in the inventive one-piece package with a release agent coating 3 applied to the plastic piece 2, said coating being appreciably less expensive than a separate release paper while simultaneously eliminating the previously unavoidable handling and disposal of a loose paper strip. The plastic piece extends laterally with portions 4,5, and longitudinally with portions 6,7 beyond the edges of the sanitary napkin.

Figure 2:
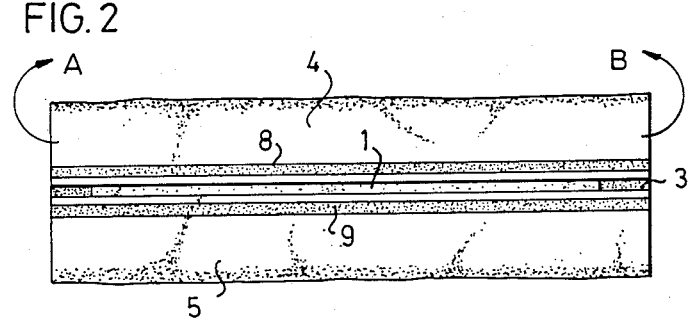
FIG. 2 illustrates the implementation of a package according to the first embodiment of a package blank shown in FIG. 1.
Figure 3:
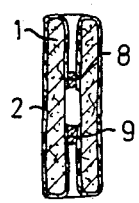

As shown in FIG. 2, the edge portions 4,5 of the plastic piece 2 are folded around each side edge and in over the opposing side of the sanitary napkin 1. In the illustrated embodiment, the side portion edges folded around the napkin generally reach up to one another. Longitudinal beads 8,9 of binding agent, preferably hot melt, are then applied close to the edges of the folded-over lateral portions 4,5 whereupon the napkin 1, together with the package blank 2, is folded around its transverse center line; this being indicated in FIG. 2 by the arrows A,B. The two halves created by folding will now be compressed causing in this way the adhesive beads 8,9 to bond together the napkin and the package blank into a coherent package. FIG. 3 is a cross-sectional view of this unit. After folding, the package unit is sealed by welding together preferably both of the end portions 6,7. To advantage, a perforation 10 is simultaneously arranged inside the welding.

In order to take out the sanitary napkin 1, the package is torn open along the perforation 10. Owing to the inwardly folded side portions 4,5 the package blank 2 will then seal tightly around the napkin, which cannot therefore be drawn straight out of the opened package. Instead, the napkin is released by turning the wrapper inside out, the pleasts in the package wall formed by the folded-in side portions 4,5 being successively stretched out. After withdrawing in this way the package blank from the napkin, the empty package blank will constitute a bag which is considerably larger as compared to its size when used as a wrapper for the napkin 1. This bag is now large enough to enclose a used sanitary napkin. Accordingly, the package blank 2 is useful both as a closely fitting wrapping around a compact package unit and as an enlarged service bag for accommodating a used napkin.

The additional embodiment of the inventive method of packaging sanitary napkins according to FIGS. 5-8 is similar to the embodiment shown in FIGS. 1-4. Thus, the details referred to in FIGS. 5-8 have been designated by the same reference numerals as corresponding details in FIGS. 1-4. These two embodiments only differ in that the package blank 2 of the embodiment shown in FIGS. 5-8 has considerably wider dimensions that that of the embodiment shown in FIGS. 1-4. Accordingly, in the embodiment of FIGS. 5-8 not only the side portions 4,5 are folded in over the napkin 1 but their edge portions 4', 5' as well are folded out towards the edges of the napkin 1. This further folding is particularly clearly seen in FIG. 7. Also in this embodiment the binder beads 8,9 are applied in the edge areas of the side portions, and more specifically, on the outwardly folded edge portions 4', 5'.

Figure 4:
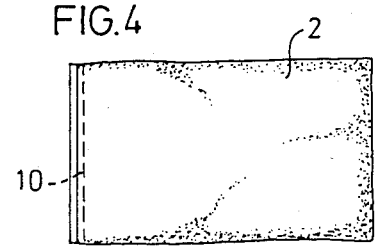
FIG. 4 is a view thereof in its completed state.
Figure 5:
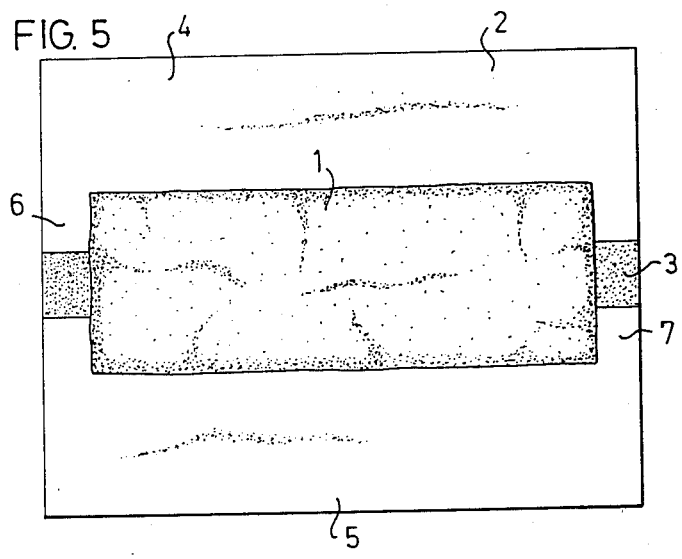
Figure 6:
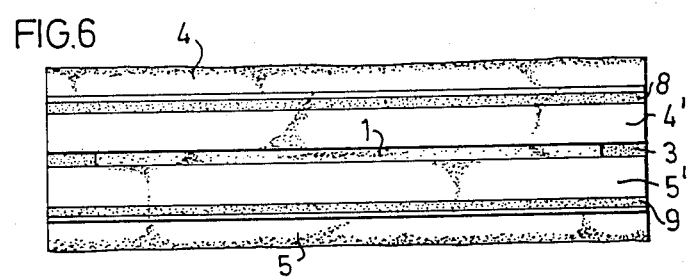
Figure 7:
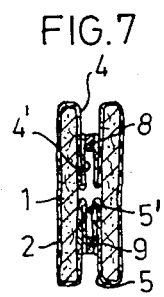
Figure 8:
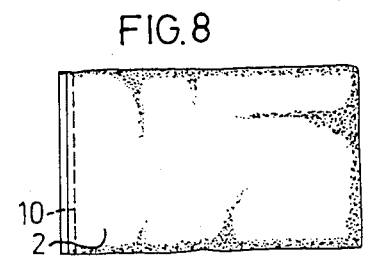

Due to the double folding of the side portions of the package blank 2, the embodiment of an inventive package shown in FIGS. 7 and 8, after opening and removal of the sanitary napkin, will provide a larger service bag than that obtained with the package shown in FIGS. 3 and 4.

In the embodiment illustrated in FIGS. 9-11 the package blank 2, which is formed of a continuously advanced unbroken web of material, is first provided with a longitudinal accordion pleat 11 by folding together its longitudinal center portion. The folded web is then coated with a longitudinally applied release agent 3 extending along either side of the accordion pleat, whereupon sanitary napkins 1 provided with adhesive beads 12,13 are superimposed while uniformly spaced on the package blank 2. The adhesive beads 12,13 serving to retain the napkins in position during use are than applied to the release coating 3. It will thus be seen from the drawings that there are two lines of adhesive 3 each contacting the napkin 1 on respectively opposite sides of the pleat and extending along the marginal folded edges, whereby the napkin itself maintains the pleat collapsed.

As shown in FIG. 10, the side portions 14,15 of the package blank extending laterally beyond the napkins are then folded around the napkins with their overlapping edges bonded together by means of a hot melt bead 16. The package blank thus wrapped around a number of napkins is finally welded together at 17 between each single napkin, and may simultaneously be cut off to form individual one-piece packages each suitably having a perforation 18 along which the package can be conveniently opened for taking out the napkin contained therein. After removal of the napkin, the package can be readily enlarged by the accordion pleat 11, located in one wall of the empty bag, being stretched open.

Figure 12:
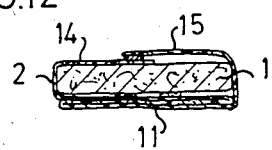
FIGS. 12 and 13 illustrate two additional embodiments of a package performed in accordance with the invention.
Figure 13:
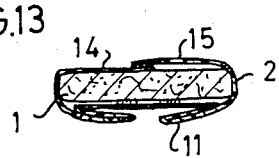

FIGS. 12 and 13 illustrte two variations of the embodiment shown in FIGS. 9-11, the only distinction being the different design of their accordion pleats 11.

Figure 14:
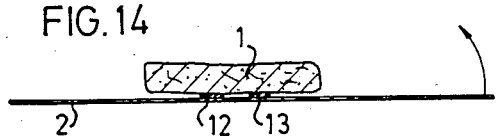
FIGS. 14–16 finally illustrating a still further embodiment of this package and the method of its manufacture.
Figure 15:
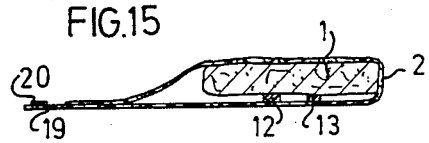
Figure 16:
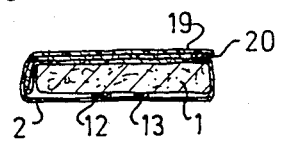

FIGS. 14-16 illustrate still another embodiment of the inventive package and the method of manufacturing it.

According to the last-mentioned embodiment, a relatively widely dimensioned package blank 2 is continuously fed along a conveyor belt (not shown), uniformly spaced sanitary napkins 1 being superimposed, as shown in FIG. 14, along the package blank and with the binder beads 12 of the napkins in abutting contact with an area of the blank 2 coated with a release agent, said area being located at least in the proximity of the blank center while extending in the longitudinal direction of the blank. Thereafter the package blank is folded as shown in FIG. 15 along with the individual napkins, and is then welded and cut between adjacent napkins in order to form detached one-piece packages.

As can be seen particularly clearly in FIG. 15, the bottom portion of the packing blank 2 folded around the napkins extends a bit 19 further out laterally than does the top portion, and to this extended area there is applied a hot melt bead 20. The blank portions extending beyond the napkins are folded in over said napkins, whereafter the package is sealed to the condition shown in FIG. 16 by means of the hot melt bead 20. When opening the package thus produced there is obained a larger bag which can be utilized as a service bag for a used napkin.

The invention is not restricted to the exemplary embodiments described in the foregoing, since a plurality of modifications are conceivable within the scope of the following claims.

For example, packages similar to those embodied as shown in FIGS. 3 and 4 could be performed otherwise than set forth above with reference to FIGS. 1 and 2. Using as a basis a plastic web having the same width in relation to the width of the napkins as that shown in FIG. 1 it would be possible, instead of folding and sealing the parcel as described with reference to FIG. 2, to weld or glue together the napkin side edges and the packing blank, subsequent to folding the packing blank and the napkin around the transverse center line of the napkin, so as to obtain a very large bag in relation to the napkin. The portions of the bag thus extending laterally beyond the napkin could then be folded into the space between the two halves of the folded napkin in order to accomplish a package similar to that shown in FIG. 3.

The package illustrated in FIG. 3 could naturally also be achieved by inserting a folded napkin right into the center of the wide bag the portions of which extending beyond the napkin then being folded in between the napkin halves for obtaining a package of the kind disclosed in FIG. 3.

We claim:

1. A package comprising in combination a disposable, fluid-absorbent sanitary article that swells upon absorption of fluid, and a fluid-impermeable sheet tightly enclosing said article, said package having opposite closed ends, at least one of said ends being openable for removing said article from said package, said package further having at least one collapsed pleat integrally formed thereform and extending between said opposite closed ends of said package, said pleat being in the form of a collapsed loop of said sheet, said pleat having marginal folded edges that lie adjacent each other and further folded edges that lie remote from each other, and two lines of adhesive each contacting said article on respectively opposite sides of said pleat and extending along and adjacent a respective said marginal folded edge, whereby the article itself maintains the pleat collapsed.

2. Package according to claim 1, wherein said package comprises a row of perforations inwardly adjacent said at least one openable end of said package.

* * * * *